Figure 2:
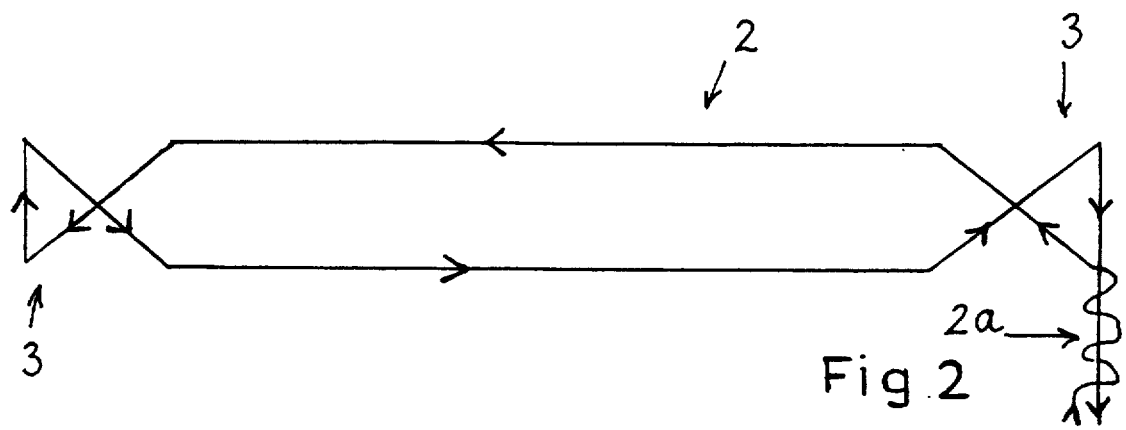

United States Patent

Guy et al.

Patent Number: 5,429,132
Date of Patent: Jul. 4, 1995

[54] PROBE SYSTEM

[75] Inventors: Christopher N. Guy; Duncan F. Gillies, both of London, Great Britain

[73] Assignee: Imperial College of Science Technology And Medicine, London, Great Britain

[21] Appl. No.: 969,254
[22] PCT Filed: Aug. 23, 1991
[86] PCT No.: PCT/GB91/01431
  § 371 Date: Feb. 22, 1993
  § 102(e) Date: Feb. 22, 1993
[87] PCT Pub. No.: WO92/03090
  PCT Pub. Date: Mar. 5, 1992

[30] Foreign Application Priority Data

Aug. 24, 1990 [GB] United Kingdom ............... 9018660

[51] Int. Cl.⁶ .................................................. A61B 5/05
[52] U.S. Cl. ...................... 128/653.1; 128/654; 128/899; 128/903; 128/656
[58] Field of Search ................ 128/653.1, 654, 658, 128/898, 899, 903, 897, 656; 340/573; 324/207.17, 207.26, 239, 329

[56] References Cited

U.S. PATENT DOCUMENTS

| | | | |
|---|---|---|---|
| 4,114,601 | 9/1978 | Abels . | |
| 4,317,078 | 2/1982 | Weed et al. . | |
| 4,431,005 | 2/1984 | McCormick | 128/653.1 |
| 4,441,210 | 4/1984 | Hochmair et al. | 128/903 X |
| 4,531,526 | 7/1985 | Genest | 128/903 X |
| 4,550,731 | 11/1985 | Batina et al. | 128/903 X |
| 5,005,592 | 4/1991 | Cartmell | 128/899 |
| 5,042,486 | 8/1991 | Pfeiler et al. | 128/658 X |
| 5,188,126 | 2/1993 | Fabian et al. | 128/903 X |
| 5,253,647 | 10/1993 | Takahashi et al. | 128/653.1 |

FOREIGN PATENT DOCUMENTS 0359697 3/1990 European Pat. Off. .
0399536 11/1990 European Pat. Off. .

Primary Examiner—Lee S. Cohen
Assistant Examiner—Brian L. Casler
Attorney, Agent, or Firm—Bell, Seltzer, Park & Gibson

[57] ABSTRACT

A probe system for use in carrying out inspections in an enclosed, non-conducting environment, such as an endoscope for use in carrying out internal inspections of a human or animal patient, comprises sensing coils (7) mounted at spaced positions along the probe (6) for movement with the latter and a planar grid array (1) of antennas (2) which is disposed adjacent the environment. AC electrical signals are supplied to the antennas, either simultaneously or sequentially, by an electrical source (4,5) so as to induce corresponding voltage signals in the sensing coils (7). When the probe (6) is introduced into the environment, the induced signals, converted to a digital format, are processed by a microprocessor (12) to produce a visual indication of the three dimensional location of the probe (6) with respect to the antenna array (1).

10 Claims, 3 Drawing Sheets

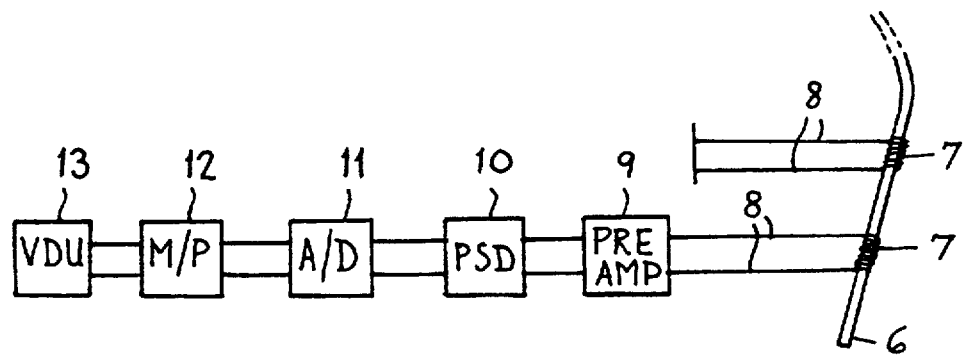
Fig.1
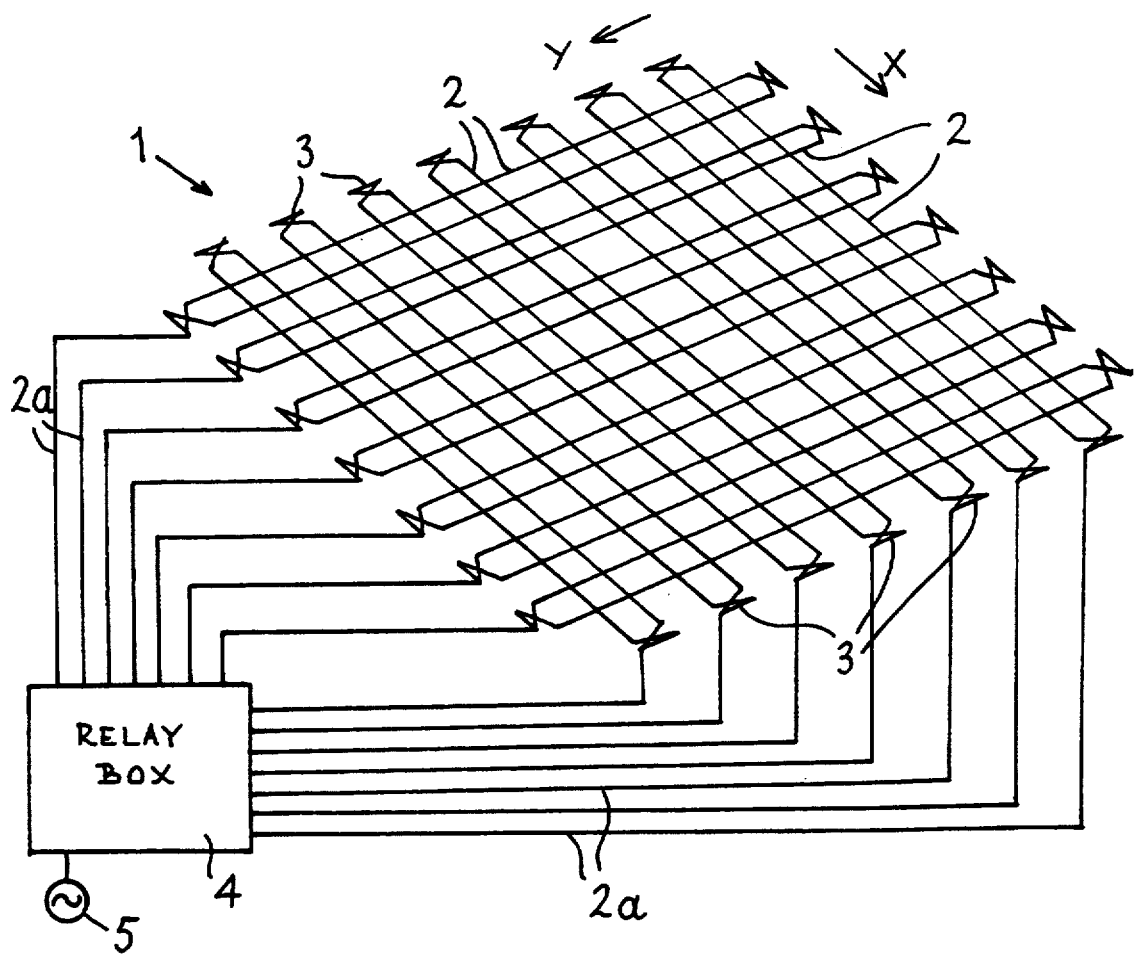

PROBE SYSTEM

This invention relates to probe systems for use in an enclosed, non-conducting environment, such as a human or animal body. Such probe systems are particularly suitable for use in endoscopy and, more particularly, colonoscopy. The invention also relates to a method of locating a probe within the body of a human or animal subject.

It is of particular importance to determine the precise location of a probe, such as an endoscope, within the body of a patient. The absence of an accurate probe locating system can cause patient complications ranging from unnecessary pain to actual perforation, instrument damage, and serious mistaken diagnosis. A further complication is that elongate probes have a tendency to form looping configurations. One probe locating technique is to employ x-ray imaging, but x-ray systems suffer from several disadvantages. They are relatively expensive and, hence, are not readily available in most endoscopic units. In addition, x-ray systems now face increasing restrictions on their use, such as protective clothing, etc. Furthermore, they produce only a relatively small two dimensional image, which is somewhat lacking in detail.

It is an object of the present invention to provide a probe system which is capable of being accurately located within an enclosed non-conducting environment, such as a human or animal body, and which does not rely on x-ray imaging for its locational information.

Accordingly, the invention consists in a probe system for use in an enclosed, non-conducting environment and including a probe having at least one sensing coil movable with the probe, an antenna array, an electrical source for supplying the antenna array with an AC electrical signal for inducing a corresponding electrical signal in the or each sensing coil, and electronic processing means connected to the sensing coil(s) for processing the induced signals and producing an indication of the three dimensional location of the probe with respect to the antenna array, characterised in that the antenna array has two sets of dipole antennas comprising elongated coils arranged in a substantially planar and mutually orthogonal array, and the electrical source is adapted to supply the AC electrical signal to each antenna coil either simultaneously or sequentially.

The invention makes use of the variation in mutual inductance between a sensing coil and the antenna array. By detecting the signals induced in the or each sensing coil by each transmitting antenna of the array, and solving field equations associated with each antenna location, the three dimensional location of the sensing coil and, hence, the probe, can be established.

In one embodiment of the invention, the sensing coil is mounted to move with the probe, which has coordinates X,Y,Z and polar angles $\theta$, $\phi$, and the planar arrays or grid of mutually orthogonal antenna coils is mounted adjacent the enclosed non-conductive environment to be accessed by the probe with the coils of the array running respectively parallel to the X and Y axes. When a single antenna coil of the grid carries an AC current signal, a voltage is induced in the sensing coil which varies in a completely defined manner with respect to the relative coordinates and the sensing coil angles. When each antenna coil of the grid is energised in turn with a short current pulse supplied from the electrical source, the sequence of signals produced by the sensing coil may be analysed to yield the sensing coil coordinates and angles. When used in endoscopic applications, the antenna array is mounted on the patient bed underneath a patient with the coils of the array running respectively parallel to the X and Y axes.

A probe, such as an endoscope, typically comprises an elongate element, in which event information concerning the location of various sections of the probe may be required. Moreover, in addition to the positional information, it may be desirable to detect the occurrence of accidental loops formed in the probe behind its tip. In one embodiment, at least one sensing coil is movable longitudinally with respect to the probe along at least a portion of its length. By moving the sensing coil along the probe and detecting its successive positions, the existence of looped configurations or other problems may be detected. Alternatively, two or more sensing coils may be mounted in spaced relationship along the length of the probe, one preferably being located adjacent the tip of the probe and the others remote from the tip. By employing such a plurality of sensing coils, data concerning the location of each portion of the probe can be obtained. Moreover, even with only two sensing coils, the relative phase of the induced signal in the two sensors, when a single antenna in the array is energised, provides information about a twist along the length of the probe and thus can be monitored to give warning of an impending loop formation. The exact location of a loop may be detected by mounting several sensors along the length of the probe. Changes in relative phase will then pinpoint which sections are twisted and, hence, looped.

With the invention, having obtained three dimensional coordinates of at least one point on the probe and at least two known points on the surface of the enclosed non-conducting environment, the electronic processing means may operate to compute an estimate of the position of the probe inside the environment. This task falls into two parts, namely, interpolating the known points to find the centre line of the probe and, secondly, estimating the tip position in the environment. The first task is relatively trivial if sufficient points are known whilst the second task is more difficult. For example, in the case of colonoscopy, although there is a great deal of variation in individual colons, there are certain anatomical properties that can be used. Hence, the sigmoid and transverse colons are known to mobile, whereas the ascending and descending colons are relatively fixed. Thus, by looking at the dynamic behaviour of different points on the endoscope, the position in the colon can be estimated. For example, if a point moves in a direction orthogonal to the endoscope body it is probable that that point is either in the sigmoid or transverse colon. Evidence can also be gained from the configuration of various parts of the endoscope. Further information is available from the inserted length of endoscope. This information must be incrementally upgraded since manoeuvres, such as pulling back to straighten the sigmoid colon, alter the relationship between the inserted length and the position of the endoscope tip. The algorithm for computing the probe position may be one in which the uncertainty is as far as possible resolved by combining several sources of information. Once the position of the tip is estimated, it is a comparatively simple matter draw the endoscope and indicate the surrounding haustral folds.

The electrical source is preferably adapted supply the antennas with AC sine wave signals having frequencies in the low to medium audio ranges, that is 1 to 10 kHz and, preferably, of the order of 2 kHz. Alternatively, the generator may be adapted to supply the antennas with radio frequency AC electrical signals.

In one convenient embodiment of the invention, for use with an endoscope, a plurality of sensing coils, for example seven, and their connecting leads are mounted at intervals inside a flexible protective plastics sheath, for example, a plastic tube approximately 2 m in length and having an external diameter less than 2.5 mm, which allows insertion of the coils into the biopsy channel of the endoscope. Location and imaging of the entire length of the scope inside a patient can thus be obtained on an unmodified endoscope by inserting the sheath into the biopsy channel and operating the sensing coil energisation sequence. In another embodiment requiring modification of a conventional endoscope, sensing coils are permanently mounted at intervals along the length of the scope. These coils are mounted substantially coaxially with the endoscope axis and are disposed between the metallic braid and the outer plastics sheath of the endoscope. With this embodiment, continuous monitoring of the endoscope location is obtained without any obstruction to the biopsy channel.

The or each sensing coil may be connectable to the electronic processing means via a preamplifier, a phase sensitive detector, which produces a demodulated DC analogue voltage correspondingly to the AC voltage signal induced in the sensing coil by the antenna array, and an analogue-to-digital (A/D) converter which digitises the coil signal for processing by the electronic processing means to produce a final graphical image. Where the probe system includes a plurality of sensing coils, each sensing coil may have its own preamplifier, phase sensitive detector and A/D converter chain or, alternatively, a multiplexing arrangement may be utilised for sequentially detecting the signal voltages induced in the sensing coils and utilising a single preamplifier, phase sensitive detector and A/D converter chain.

The antenna array is in the form of a substantially planar grid or matrix with some or all of the antenna of the array comprising dipole antennas. The use of dipole antennas reduces the signal contribution from the wire leads and the return wire.

The planar array of antennas may, for example, comprise two orthogonal sets of seven or more long thin dipole coils. Each set provides enough data to compute the Z (height) and either X or Y components of the or each sensing coil position with respect to the array. This configuration in conjunction with the electronic processing means allows for a rapid computation of sensing coil position because the X and Y coordinates are separately determined.

Small errors in position may be produced by dipole coils having plain, short ends because these sections on, for example, the Y coils, produce small but defined contributions to the X component of the field and these contributions are not taken into account in the computation produced by the electronic processing means. In order effectively to reduce these contributions, the ends of the coil turns may be specially configured as so called "butterfly" end windings which alter an effective short single wire section into a dipole perpendicular to the longitudinal axis of each coil. The field from such an arrangement falls off with distance more rapidly than that of a single wire and thus the field contribution of the ends is very much reduced.

The electrical source for supplying AC electrical signals to the antenna array may be adapted simultaneously to energise each of the plurality of antenna coils with a distinct or individual frequency. In this way, the time taken to establish the location of the probe may be reduced as all the antenna coils are transmitting simultaneously, each with its own distinctive frequency. Where the time taken to interrogate the or each sensing coil is not critical, the electrical source may operate at a single frequency energising each of the antenna coils in turn.

The present invention also consists in a method of locating a probe within the body of a human or animal subject, comprising the steps of inserting the probe into the body of the subject, said probe having at least one sensing coil movable therewith, disposing an antenna array adjacent the subject, said antenna array having two sets of dipole antennas comprising elongated coils arranged in a substantially planar and mutually orthogonal array, energising each of the antenna coils, either simultaneously or sequentially, with an AC electrical signal, detecting the resulting signal induced in the or each sensing coil, and processing the detected signal(s) to produce an indication of the three dimensional location of the probe with respect to the antenna array.

Preferably, the method includes the further step of detecting the signals induced in one or more reference coils externally of the body of the subject, in order to establish the location of the body of the subject with respect to the antenna array.

Figure 3:
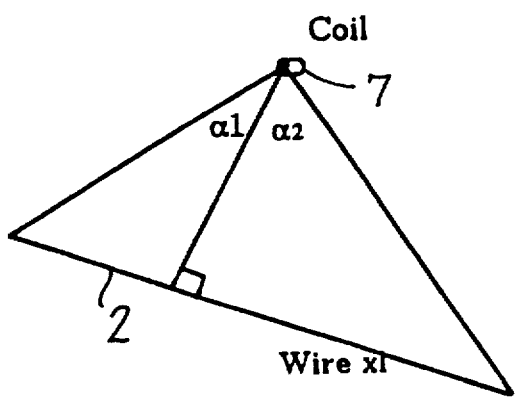
Figure 4:
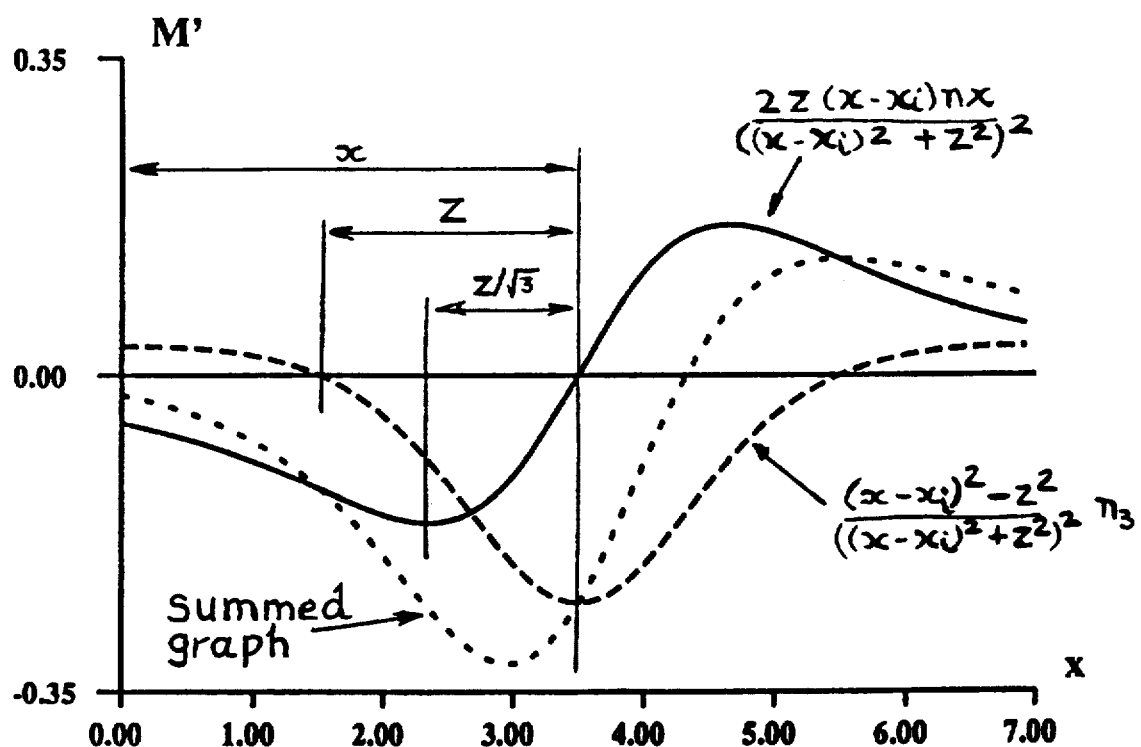

In order that the present invention may be more readily understood, reference will now be made to the accompanying drawings, in which:

FIG. 1 schematically illustrates one embodiment of the invention,

FIG. 2 schematically illustrates the winding configuration of each dipole antenna of the antenna grid, FIG. 3 is a diagram utilised in applying a correction to the field equations in order to take into account the fact that the antenna wires are of finite length, and FIG. 4 is a graph illustrating the variation in the two components of the equation on which is based the algorithm for solving the field equations.

Referring to FIG. 1 of the drawings, the probe system includes an array 1 of dipole antennas 2 in the form of a planar grid comprising two mutually orthogonal sets of seven elongated thin coils extending in X and Y directions. Each dipole antenna 2 may, for example, comprise a copper coil having twenty turns and typically have dimensions of 100 cm×5 cm. The spacing between the antennas 2 within the grid array 1 is typically 7.5 cm.

As illustrated in FIG. 2, the ends 3 of each turn of a dipole antenna coil 2 are specially configured. The reason for this is that small errors in position would be produced by coils with plain short ends because these sections, for example, on the Y coils produce small but defined contributions to the X component of the field. By providing the turns with so-called "butterfly" end windings, as illustrated, these undesirable field contributions are effectively reduced. In effect, this arrangement alters a short single wire section at each end into a net dipole perpendicular to the longitudinal axis of the associated coil.

Each antenna 2 is connected via twisted leads 2a to a relay box 4 which is adapted sequentially to connect each antenna with an AC signal generator 5. In one example, the generator 5 is capable of generating a 9 kHz sine wave signal having a peak current of 50 mA.

Associated with the antenna array 1 is an endoscopic probe 6 having seven sensing coils 7 mounted coaxially with the probe at spaced positions along its length, one of the sensing coils being mounted at or adjacent the tip of the probe. For the sake of convenience, only two coils 7 are illustrated. Each sensing coil 7 is wound about the probe between the metallic braid and the outer plastic sheath of the probe and typically comprises 800 turns of fine copper wire (48 swg) on a tubular Mu metal core which is a commercially available soft ferro magnetic material with a high relative permeability (in the range 10,000–100,000). Each sensing coil 7 is connected via a screened twisted cable pair 8 to a preamplifier 9 which is in turn connected to a phase sensitive detector 10 for producing a DC voltage level proportional to the amplitude of the AC voltage induced in the associated sensing coil 7. The signals from the phase sensitive detector 10 are fed to an A/D converter 11 which produces digital signals dependent on the DC signal level at the output of the phase sensitive detector for processing by a microprocessor 12 and subsequent display on a video display unit 13 associated with the microprocessor. Only the chain of circuits 9,10 and 11 associated with one sensing coil 7 is illustrated in FIG. 1.

In using the system of FIG. 1 for conducting an endoscopic inspection of a cavity or passage, for example, the colon, in the body of a human or animal patient, the planar antenna array 1 is disposed underneath the patient on the patient's bed. Conveniently, the antenna array is formed by winding the multi-turn coils of the antennas 2 in grooves cut accurately in a single large board that forms part of the patient's bed. Thus, the array is permanently in place and does not hinder the positioning and turning of the patient during an endoscopic procedure. Having positioned the patient on the antenna array, the endoscopic probe 6 is inserted into the colon of the patient, whereafter, each antenna 2 is energised in turn by the AC electrical source constituted by the relay box 4 and generators. The resulting signals induced in the sensing coils 7 are fed to the microprocessor 12 via the chain of circuits 9, 10 and 11 and the microprocessor interprets the signals in terms of the three dimensional locations of the probe. The X,Y and Z coordinates and the axial direction vector of each coil 7 can be established by comparing the signals induced from each antenna 2 and by solving certain field equations associated with each antenna location.

Additional sensing coils (not shown) may be placed in predetermined positions on the patient's body (body markers) so that the position of the torso can be estimated with respect to the array 1 which serves as a common reference frame. By this means, the position and configuration of the endoscope with respect to the patient's anatomy can be computed.

The determination of sensing coil positions by the microprocessor relies on the integral equation for the mutual inductance between two coils. For a general coil arrangement the equation (Von Neumann's formula) does not allow the direct determination of sensing coil coordinates from measurement of mutual inductance. For the purposes of the present invention, therefore, this is simplified in the following ways:

(i) Each sensing coil 7 has a small area and thus it can be considered to be a point magnetic induction detector.

(ii) The antenna array 1 separates the determination of the X and Y components. For each set of dipoles 2 (X and Y) the signal is insensitive to sensing coil position along the longitudinal axis of each set.

(iii) The width of each coil (dipole is sufficiently small) that the field produced by each antenna can, to a good approximation be considered as the derivative with respect to wire location of the field due to a long single wire.

Even with these simplifications there is no exact analytic method for the determination of X, Y, Z coordinates of a sensing coil. Rather approximate iterative schemes have to be employed. Applicants method has two steps:

(a) The first step makes use of the spatial properties of the functions described below in order to get a first estimate of the X,Y,Z coordinates from the mutual inductance measurements associated with respectively the X and Y dipole sets. This very much reduces the range over which the second stage has to search in order to fit the model equations to the data.

(b) In the second step, an iterative algorithm searches the reduced region of the X,Y axes checking at each stage that the revised estimates provide a better fit to the data.

In this scheme two independent estimates of Z are obtained and these can be used as a check on the accuracy of the final estimates.

The following is a more detailed description of steps (a) and (b).

Hence, the equations to be solved are:

The equation for the mutual inductance between an infinitely long straight wire, parallel to the Y axis at coordinate xi, and a coil 7 at coordinate x,y,z is:

$$M_i = (n_x z + n_z(x_i - x))/((x_i - x)^2 + z^2) \quad (1)$$

where $[n_x, n_y, n_z]$ is a vector in the axial direction of the coil whose magnitude is dependent on the current in the wire, and the size and number of turns of the coil. A similar equation relates mutual inductance to position for wires parallel to the X-axis.

For the case of a dipole 2 replacing the infinite wire, we make the approximation that the mutual inductance is the differential of the equation for magnetic flux induced in coil B when a current i flows in a coil A (that is $\phi_A = M_{AB} i_B$) with respect to x, which yields $$M_i' = (2n_x z(xi - x) + n_z((x_i - x)^2 - z^2))/((x_i - x)^2 + z^2)^2 \quad (2)$$

It is also convenient to consider the second differential of Mi, since the stationary points of the dipole equation are of interest. It is:

$$M_i'' = (2n_x z(3(xi-x)^2 - z^2) + 2n_z(x_i-x)((x_i-x)^2 - 3z^2))/((x_i-x)^2 + z^2)^3 \quad (3)$$

The above equations assume that the wire length is infinite. However, in any practical application finite wires are used. A correction can be made to account for the fact that the induced voltage is less. Hence, referring to FIG. 3, if α1 and α2 are the angles between lines joining a coil 7 to the ends of the transmitting wire and the perpendicular from the coil to the wire, then the induced voltage is reduced by:

$$2/(\sin(\alpha 1) + \sin(\alpha 2)) \quad (4)$$

A direct solution to the single wire equation is available. It is found by multiplying out equation (1) to give:

$$2M_jx_ix - M_i(z^2+x^2) + x_in_z + n_xz - n_zx - M_jx_i^2 = 0 \quad (5)$$

if we make the substitutions:

$$s1 = (z^2 + x^2) \quad (6)$$

$$s2 = (n_xz - n_zx) \quad (7)$$

we obtain a linear equation in four variables, x,nx,s1 and s2, which can be solved with four readings (i=0,1,2,3) from four wires. The values of z and nz can be obtained from the simple quadratic equations (6) and (7) after solution of the four linear equations.

An experimental system has been devised to try this solution method, using an area of 100 sq. cm., and it was found to work well for values of z greater than 5 cm. It is believed that with further attention to the computation a stable solution could be obtained by this method over the required operating range.

Since this method depends critically on the relative magnitudes of the readings taken from the individual wires, the finite length $\alpha$ correction factors must be applied. Addition of these correction factors raises the order of this solution such that it becomes incomputable directly. However, an iterative scheme can be applied simply, as follows:

(i) Compute an estimate of the position of a sensing coil 7 using the direct linear solution.

(ii) For each measurement, compute the $\alpha$ correction based on the coil's estimated position. Correct the measured value by the inverse of this factor.

(iii) Recompute the estimate of the sensing coil position.

(iv) If the new estimate is sufficiently close to the old estimate then terminate, otherwise go to step (ii).

This algorithm has been found to work satisfactorily with simulated data. However, further investigation has been suspended in view of the better results obtained using dipole antennas 2 rather than single wires.

Although there are only four unknowns in the dipole equation (2), the fourth order terms means that a direct solution is not available from four sets of readings.

The fourth order terms in the dipole equation means that, despite the fact that there are only four unknowns, a solution cannot be obtained directly from four measurements. Either an iterative solution must be used, or an over specified system of equations is required. The latter may be done by the same method outlined above. Multiplying out the dipole equation, and grouping the terms with common coefficients, we obtain:

$$M_jx_i - 4M_jx_i^2(3x^2+z^2) - 4M_jx_i(x^3 + xz) + M_i(x^4+z^4 + 2x^2z^2) - x_i^2nz + 2x \cdot (n_zx - n_xz) + (2n_xzx + n_zx^2) = 0 \quad (8)$$

as before we can linearise equation (3) by substituting:

$$s1 = (3x^2 + z^2) \quad (9)$$

$$s2 = (x^3 + xz) \quad (10)$$

$$s3 = (x^4 + z^4 + 2x^2z^2) \quad (11)$$

$$s4 = (n_zx - n_xz) \quad (12)$$

$$s5 = (2n_xzx + n_zx^2) \quad (13)$$

to obtain a system of equation in seven variables (x,nz,s1, s2,s3,s4,s5). After solution values for z and nx may be obtained from further solution of equations (9-13). This solution has not been tested for the following reasons. Firstly, since it depends on the magnitudes of the seven measured points, it is necessary to correct for the finite lengths of the dipoles. This requires an iterative process which includes a gaussian elimination on a seven by seven matrix and, consequently, is computationally very slow. Secondly, the presence of fourth order terms makes the method less robust against error.

Accordingly, a fast iterative algorithm has been developed for solution of the field equations. It can be formulated for both single wires or dipoles. By way of example, the latter form is presented below.

The algorithm is based on the fact that the equation is a linear combination of two components:

$$2z(xi-x)/((x_i-x)^2+z^2)^2 \quad (14)$$

and $$(x_i-x)^2-z^2))/((x_i-x)^2+z^2)^2 \quad (15)$$

These are shown in FIG. 4. The nz component has a peak at the position of the coil and zeros at a distance of z from the peak, and the nx component has a zero at the same place, and two peaks at a distance $z\sqrt{3}$ from the position of the coil. In FIG. 4, the curves are drawn assuming positive nx and nz. Summing these two curves, the resulting graph must have a zero to the right of the peak, at the point where the positive (nx) component equals the negative (nz) component. This zero must occur at a distance of less than, z from the position of the coil. The summed graph must also have a peak to the left of the coil position. It will occur when the negative slope of the nz-component is equal to the positive slope of the nx-component. This will be somewhere between the coil position, where the slope of the nz component is zero, and the negative peak of the nx trace, where its slope falls to zero. Hence, the peak is at most $z\sqrt{3}$ from the coil position. The summed curve will also have a smaller peak at a distance of greater than z to the right of the coil, and possibly another peak and zero to the left of the coil. It is clear to see that (for nz>0) these peaks must be smaller in magnitude than the one close to the root close peak, since the amplitude of both traces fall off sharply with distance from the coil position. Similarly, it is clear to see that the other zero, if present, is further from the main peak. Hence, for a give set of measurements, it is known that the coil is located between the largest peak and its closest zero, which are closer together than $z(1+1/\sqrt{3})$. Similar arguments apply to the cases where nx and nz are both negative, or of different signs.

The algorithm is a binary search of the space between the largest peak and its closest zero. If an estimate is made of the coil position, say xc, and we write:

$$uz = xc - xz \quad (16)$$

$$up = xc - xp \quad (17)$$

where xz and xp are the positions of the peak and the zero, then the following equations result:

$$Mg = n_z/z^2 \quad (18)$$

$$Mp = (2n_x z \, up + nz(up^2 - z^2))/(up^2 + z^2) \quad (19)$$

$$2n_x z \, uz = -nz(uz^2 - z^2) \quad (20)$$

$$2n_z z(3up^2 - z^2) = 2n_z up(up^2 - 3z^2) \quad (21)$$

For the most accurate estimate, equations (18), (20) and (21) can be solved to provide an estimate for nx,nz and z. The resulting graph is then compared with the real data. For points outside the peak to nearest zero span, an estimate too close to the zero results in the estimated magnitudes being too high, and vice versa, which gives a simple criterion for choosing how to improve the estimate xc, by binary search. Equation (19) was used as an alternative to equation (21) in the current study. It has the advantage that the position of the peak need not be known, any magnitude will suffice. However, it produces a less accurate solution, since it depends on a measured magnitude, at or near to the peak, and hence requires compensation for the finite dipole lengths. Note that the positions of the peaks and zeros are not altered by the dipole lengths.

Two problems have been found with the method described above. Firstly, in some cases it is possible that the closest zero is not within the measured range. This can be partly solved by extrapolation of the measured data, but this technique is error prone, and therefore undesirable. If the measured range is extended by the maximum operating height beyond the position range in which the coil is to be located, then this problem will never arise. This is possible for the endoscope application in one dimension. Having solved for that direction, use can be made of the known value of z to provide a more accurate extrapolation in the other direction.

The second problem is caused when the values of nx and nz are both close to zero. In this case very low measurements are obtained. This condition can be identified, since in the orthogonal direction the trace has a clearly defined zero with symmetrical peaks. One possible solution in this case is to use an alternate set of coils, configured to provide the localisation for this special case. Since everything about the coil, except its x (or y) coordinate is known, this arrangement can be kept very simple.

Whilst a particular embodiment has been described, it will be understood that modifications can be made without departing from the scope of the invention, as defined by the appended claims. For example, whilst a seven by seven antenna array 1 is shown and described, larger planar grid arrays are possible. Moreover, instead of mounting the sensing coils 7 at fixed positions about the endoscopic probe, one or more coils with connecting leads for coupling to associated preamplifiers may be disposed at intervals inside a protective plastics sheath capable of being inserted and moved longitudinally of the probe along the biopsy channel of the endoscope. Instead of providing each sensing coil 7 with its own individual chain of circuits 9, 10 and 11, a multiplexing system may be used sequentially to connect the sensing coils to a single such chain. The microprocessor 12 may control switching of the relay box 4 to produce energisation of the dipole antennas 2 of the array 1 in a predetermined sequence.

We claim:

1. In a probe system for use in an enclosed, nonconducting environment and including a probe having at least one sensing coil movable with said probe, an antenna array, an electrical source for supplying said antenna array with at least one AC electrical signal for producing corresponding induced electrical signals in said at least one sensing coil, and electronic processing means connected to said at least one sensing coil for processing said induced signals and producing an indication of the three-dimensional location of said probe with respect to said antenna array, the improvement comprising said antenna array wherein said array has two sets of dipole antennas comprising elongated coils arranged in a substantially planar and mutually orthogonal array, and said electrical source includes means for supplying said at least one AC electrical signal to said antenna coils either simultaneously or sequentially.

2. A probe system according to claim 1, wherein said electrical source includes means for supplying said antenna coils with at least one audio frequency AC electrical signal.

3. A probe system according to claim 1 or 2, wherein said probe is an elongated element and said at least one sensing coil includes a plurality of sensing coils disposed at spaced positions along the length of said probe.

4. A probe system according to claim 1, wherein said probe is an endoscope having a biopsy channel and said at least one sensing coil is disposed in the biopsy channel of said endoscope.

5. A probe system according to claim 1, wherein said at least one sensing coil is mounted on said probe substantially coaxially therewith.

6. A probe system according to claim 1, including phase sensitive detector means for producing a demodulated DC analog voltage proportional to said induced electrical signals in said at least one sensing coil, and said at least one sensing coil is connected to said processing means via said phase sensitive detector means.

7. A probe system according to claim 6, including preamplifying means connecting said at least one sensing coil to said phase sensitive detector means, and A/D converting means connecting said phase sensitive detector means to said processing means for converting said DC voltage produced by said detector means into digital signals for processing by said processing means.

8. A probe system according to claim 1, wherein said electrical source includes means for simultaneously supplying each said antenna coil of said antenna array with an AC electrical signal of distinct frequency.

9. A method of locating a probe within the body of a human or animal subject, comprising the steps of inserting said probe into the body of said subject, said probe having at least one sensing coil movable therewith, disposing an antenna array adjacent said subject, said antenna array having two sets of dipole antennas comprising elongated coils arranged in a substantially planar and mutually orthogonal array, energizing said antenna coils, either simultaneously or sequentially, with at least one AC electrical signal, detecting resulting signals induced in said at least one sensing coil, and processing said detected signals to produce an indication of a three-dimensional location of said probe with respect to said antenna array.

10. A method according to claim 9, further comprising the step of electronically establishing the position of the body of said subject with respect to said antenna array thereby to enable computation of the position and configuration of the probe with respect to said body.

* * * * *

UNITED STATES PATENT AND TRADEMARK OFFICE
CERTIFICATE OF CORRECTION

PATENT NO. : 5,429,132

DATED : July 4, 1995

INVENTOR(S) : Christopher N. Guy and Duncan F. Gillies

It is certified that error appears in the above-indentified patent and that said Letters Patent is hereby corrected as shown below:

Column 2, line 65, after "matter" insert -- to --.

Column 2, line 67, after "adapted" insert -- to --.

Column 7, in line 2 of Equation 8, after "4" (second occurrence) insert -- + --.

Column 8, line 35, after "than" omit a comma (,).

Column 8, line 43, "z√3" should be -- z/√3 --.

Column 9, Equation 21, "$2n_z^z$" should be -- $2n_x z$ --.

Column 9, Equation 21, after "=" insert a dash (-).

Signed and Sealed this

Seventeenth Day of October, 1995

Attest:

*Attesting Officer*

BRUCE LEHMAN

*Commissioner of Patents and Trademarks*